(12) United States Patent
Zilla et al.

(10) Patent No.: US 7,022,135 B2
(45) Date of Patent: Apr. 4, 2006

(54) FILM WITH HIGHLY POROUS VASCULAR GRAFT PROSTHESES

(75) Inventors: Peter Paul Zilla, Camps Bay (ZA); Deon Bezuidenhout, Vredehoek (ZA); Jacobus Petrus Theron, Stellenbosch (ZA)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/219,843

(22) Filed: Aug. 15, 2002

(65) Prior Publication Data

US 2003/0045927 A1 Mar. 6, 2003

Related U.S. Application Data

(60) Provisional application No. 60/313,075, filed on Aug. 17, 2001.

(51) Int. Cl.
*A61F 2/06* (2006.01)

(52) U.S. Cl. .................... 623/1.39; 623/1.46
(58) Field of Classification Search ....... 623/1.39–1.48
See application file for complete search history.

(56) References Cited

U.S. PATENT DOCUMENTS

| | | | |
|---|---|---|---|
| 4,605,406 A | 8/1986 | Cahalan et al. | |
| 4,731,073 A | 3/1988 | Robinson | |
| 4,747,848 A | 5/1988 | Maini | |
| 4,770,664 A | 9/1988 | Gogolewski | |
| 4,784,659 A | 11/1988 | Fleckenstein et al. | 623/1 |
| 4,816,339 A * | 3/1989 | Tu et al. | 428/421 |
| 4,871,361 A | 10/1989 | Kira | |
| 4,892,539 A | 1/1990 | Koch | |
| 4,955,899 A | 9/1990 | Della Corna et al. | |
| 5,152,782 A | 10/1992 | Kowligi et al. | |
| 5,219,662 A | 6/1993 | Grimminger et al. | |
| 5,292,333 A | 3/1994 | Johnson | |
| 5,298,276 A | 3/1994 | Jayaraman | |
| 5,415,619 A | 5/1995 | Lee et al. | |
| 5,824,050 A * | 10/1998 | Karwoski et al. | 623/1.4 |
| 5,851,229 A * | 12/1998 | Lentz et al. | 623/23.72 |
| 5,869,127 A | 2/1999 | Zhong | |
| 5,879,383 A * | 3/1999 | Bruchman et al. | 623/2.42 |
| 6,028,164 A | 2/2000 | Loomis | |
| 6,117,425 A | 9/2000 | MacPhee et al. | |
| 6,121,341 A | 9/2000 | Sawhney et al. | |
| 6,132,473 A | 10/2000 | Williams et al. | |
| 6,136,024 A | 10/2000 | Shimizu | |
| 6,162,247 A | 12/2000 | Weadock et al. | |
| 6,166,130 A | 12/2000 | Rhee et al. | |
| 6,177,609 B1 | 1/2001 | Castro et al. | |

(Continued)

FOREIGN PATENT DOCUMENTS

EP 0 495 127 7/1992

(Continued)

OTHER PUBLICATIONS

Kito, H. et al., "Differentiated biocompatible design of luminal and outer graft surfaces. Photocurable extracellular matrices, fabrication and cellular response" ASAIO Journal, vol. 39, No. 3, 7-9/1993, pp. M506-M511.

(Continued)

*Primary Examiner*—Suzette J-J Gherbi
(74) *Attorney, Agent, or Firm*—Fredrikson & Byron, P.A.

(57) ABSTRACT

A vascular graft prosthesis having ingrowth-permissive lumenal wall features with a thin film or layer of sealant-like material placed at a lumenal wall location to promote improved transmural tissue growth and healing.

46 Claims, 5 Drawing Sheets

U.S. PATENT DOCUMENTS

| | | | |
|---|---|---|---|
| 6,187,038 B1 | 2/2001 | Sullivan et al. | |
| 6,192,944 B1 | 2/2001 | Greenhalgh | |
| 6,217,894 B1 | 4/2001 | Sawhney et al. | |
| 6,231,605 B1 | 5/2001 | Ku | |
| 6,368,347 B1* | 4/2002 | Maini et al. | 623/1.46 |
| 6,376,573 B1* | 4/2002 | White et al. | 523/115 |
| 6,428,571 B1* | 8/2002 | Lentz et al. | 623/1.4 |
| 6,436,135 B1* | 8/2002 | Goldfarb | 623/1.39 |
| 6,443,941 B1* | 9/2002 | Slepian et al. | 604/522 |
| 6,517,571 B1* | 2/2003 | Brauker et al. | 623/1.13 |
| 6,521,284 B1* | 2/2003 | Parsons et al. | 427/2.24 |
| 6,743,253 B1* | 6/2004 | Phaneuf et al. | 623/1.46 |
| 2003/0105510 A1* | 6/2003 | DiMatteo et al. | 623/1.13 |
| 2004/0197501 A1* | 10/2004 | Sridharan | 428/35.2 |

FOREIGN PATENT DOCUMENTS

| | | |
|---|---|---|
| WO | WO 0/ 05333 | 1/2001 |

OTHER PUBLICATIONS

Sasajima, T., et al., "Myristoyl gelatin as a sealant for Dacron vascular prostheses" Official Journal of the International Society for Artificial Organs, vol. 21, No. 4, Apr. 1997, pp. 287-292.

Bense, C.A. et al., "Plasmin degradation of fibrin coatings on synthetic polymer substrates" Journal of Biomedical Materials Research, vol. 46, No. 3, 1998, pp. 305-314.

Nojiri, C. et al., "Blood compatibility of PEO grafted polyurethane and HEMA/styrene block copolymer surfaces" Journal of Biomedical Materials Research, vol. 24, No. 9, Sep. 1990, pp. 1151-1171.

Lumsden, A.B., "Nonporous silicone polymer coating of expanded polytetrafluoroethylene graft neointimal hyperplasia in dog and baboon models" Journal of Vascular Surgery, vol. 24, No. 5, Nov. 1996, pp. 825-833.

Granke, K. et al., "Analysis of graft healing in a new elastomer-coated vascular prosthesis" Cardiovascular Surgery, vol. 1, No. 3: pp. 254-261, believed to be available prior to the filing date of the instant application.

Nojiri, C. et al., "Nonthrombogenic polymer vascular prosthesis" Official Journal of the International Society for Artificial Organs, vol. 19, No. 1, Jan. 1995, pp. 32-38.

Aldenhoff, Y.B. et al., "Performance of a polyurethane vascular prosthesis carrying a dipyridamole (Persantin) coating on its lumenal surface" Journal of Biomedical Materials Research, vol. 54, Dec. 1999, pp. 224-233.

Phaneuf, M.D. et al, "Coating of Darcon vascular graft with an ionic polyurethane: a novel sealant with protein binding properties" Biomaterials, Mar. 2000 22: pp. 463-469.

Uretzky, G. et al., "Long-term evaluation of a new selectively biodegradable vascular graft coated with polyethylene oxide-polylactic acid for right ventricular conduit. An experimental study" Thoracic and Cardiovascular Surgery, vol. 100, No. 5, Nov. 1990, pp. 769-776.

* cited by examiner

FILM WITH HIGHLY POROUS VASCULAR GRAFT PROSTHESES

RELATED APPLICATION

This application claims priority to provisional U.S. application Ser. No. 60/313,075, filed Aug. 17, 2001.

FIELD OF THE INVENTION

This invention relates to improved structures for vascular graft prostheses.

BACKGROUND OF THE INVENTION

A range of vascular grafts are utilized within the medical arts fields, but often such grafts do not permit sufficient healing due to many reasons. In particular, small diameter conventional vascular grafts do not permit sufficient tissue ingrowth or transmural endothelialization that would allow for proper healing and satisfactory long-term outcomes. Larger bore grafts often are too stiff and do not have proper ingrowth of surrounding tissue. Various approaches have been attempted to overcome these deficiencies in the prior art, with relative lack of success. This invention is designed to provide solutions to these serious and long misunderstood problems.

BRIEF SUMMARY OF THE INVENTION

A vascular graft prosthesis has a polymeric tubular structure. The structure has a porous wall with interstices arranged to permit transmural ingrowth of tissue substantially through the full thickness of the wall. A thin film or layer of sealant material is on a portion of the wall forming a lumenal wall surface which promotes rather than inhibits transmural tissue growth.

DETAILED DESCRIPTION OF THE INVENTION

Figure 1:
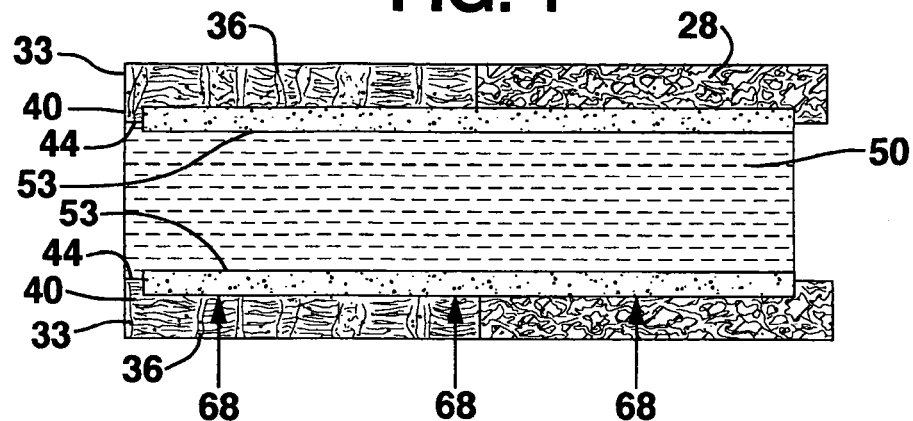
FIG. 1 is a sectional schematic view of a segment of a hybrid graft model illustrating fibrin buildup.
Figure 2:
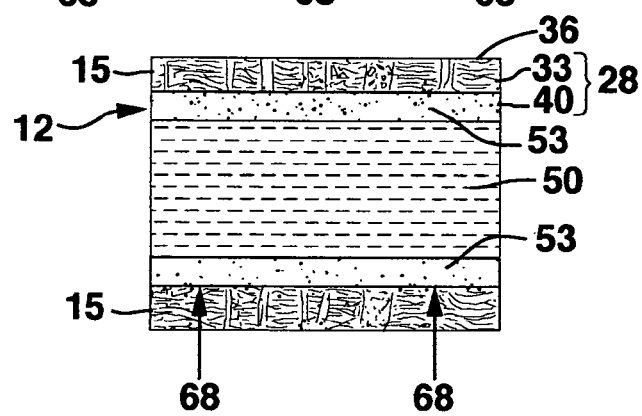
FIG. 2 is a sectional schematic view of a segment of an ePTFE graft model illustrating fibrin buildup.
Figure 3:
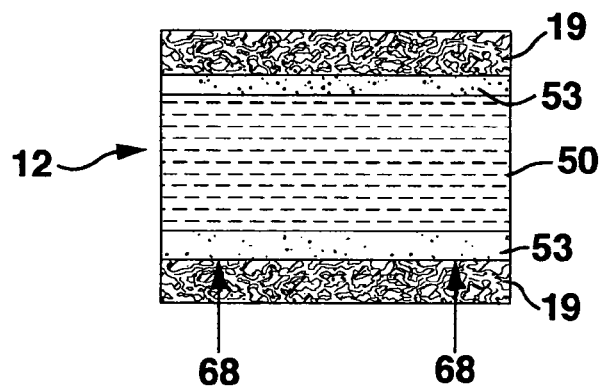
FIG. 3 is a sectional schematic view of a segment of a polyurethane graft model illustrating fibrin buildup.
Figure 4:
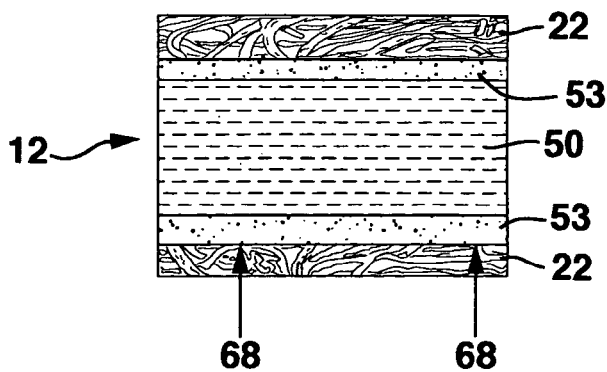
FIG. 4 is a sectional schematic view of a segment of a polyethylene terephthalate (e.g. Dacron) graft model illustrating fibrin buildup.

Various coatings and graft-related surface applications are known, but none have been utilized or specifically designed according to the technology disclosed herein, nor have any been functionally appropriate for achieving the excellent results to overcome the problems of the prior art. Conventional vascular graft prostheses do not permit sufficient tissue ingrowth or transmural endothelialization that would allow for proper healing and satisfactory long-term outcomes. This is partly due to a failure of past designers to recognize certain mechanisms and partly due to inadequate materials to assemble or manufacture the proper structures. For example, a 30 μm expanded polytetrafluoroethylene (ePTFE) graft has been shown to not support full transmural healing due to the fact that the capillaries (10–15 μm in diameter), the smallest vessels required to sustain tissue in the graft wall, simply are not able to grow in to the full extent of the wall. This is due to the tight packing of internodular fibrils. Thus, although the internodular distance may be 30 μm, the actual ingrowth dimensions are much lower (probably in the range of 5–10 μm). In addition, the lack of defined channels (interconnections between "pores") of sufficient porosity results in the "tapering down" of ingrowth spaces as one progresses into the wall. A similar analysis may be made for tightly woven fabric grafts (such as, for example, the material known as Polyethylene terephthalate (also referred to herein by its trade name "Dacron")). Further, the similar problem exists in foam type structures described in the prior art, such as those fabricated from polyurethane. The definition of these polyurethane graft pore dimensions is rather difficult, as the pores are irregular in shape and size, and generally have poor interconnectivity. In addition many of them have impermeable (at least to tissue) skins on either or both the ablumenal and lumenal sides.

Consequently, the attendant space restrictions within the structures of artificial grafts create a hostile environment for desired tissue ingrowth. These space restrictions are caused by two main factors. The first factor is the physical structure of the graft wall material. Typically, there is inadequate spacing for capillaries to grow transmurally into the graft beyond only one outer portion. The second factor is the filling of the inner lumenal portion of the graft wall by either blood products or artificial sealant materials. In either case, the clogging of the inner portion of the wall structure creates a growth-prohibitive environment that prevents desired healing.

Two types of angiogenesis are desirable for spontaneously healing of vascular grafts. A pure capillary ingrowth with the goal of surface endothelialization (with a space requirement of greater than about 10μ in continuity) is one type. A second type is arteriole ingrowth with a goal of surface endothelialization plus arterialization of the prosthetic vessel wall (with a space requirement of about 23μ in continuity). In addition to the arterialization of capillary walls, the population of the pores by smooth muscle cells and other desirable cell and extracellular matrix tissues is required for long-term healing and other performance characteristics, such as flexibility and compliance.

Although synthetic grafts have been shown to endothelialize by transanastomotic outgrowth in some animal models, notably canine, it is well known that this type of outgrowth in humans is limited to 1–2 cm (peripheral graft length up to 60 cm). The goal of Applicants is, therefore, to achieve transmural ingrowth of endothelial cells and subsequent confluent endothelialization of the graft lumen.

This invention discloses short- and long-term strategies to overcome this healing problem, for both large and small diameter grafts. One short-term strategy includes use of a permanent sealant or film on a very high porosity graft material, such as highly porous expanded polytetrafluoroethylene (ePTFE). One long-term solution includes use of a temporary sealant on porous polyurethane grafts with angiopermissive porosity. It is recognized that other combinations of short-term and long-term solutions are contemplated and possible within this invention. Overall, however, the lack of healing in commercial grafts can be ascribed to the insufficient size of the ingrowth spaces. Due to the irregular structure of the pores (between the nodes and internodular fibers), the available ingrowth spaces rapidly narrow down to sub-arteriole dimensions. It is known that increasing the internodal distances in grafts to 45, 60 and 90 μm respectively, has been attempted, but without significant improvement in healing response. Further, various "foam type" experimental prostheses have also been developed from elastomeric materials in order to increase the ingrowth spaces and attain compliance matching with natural vessels. These prostheses also failed to show sufficient healing due to a variety of factors, including small pore sizes, limited interconnectivity between pores and permanent (impermeable) ablumenal and/or lumenal skins. Also, various sealants have been used in vascular prostheses, and possibly without appreciating the adverse effects these sealants have on the healing process. These include, for example, hemostatic impregnation of the graft wall with collagen, fibrin or gelatin in order to prevent excessive blood flow through the wall during implantation, and coating of the surfaces of grafts with elastomers or growth inhibitors, etc., for reasons other than to improve transmural healing and in manners adverse to healing.

Conventional ePTFE and Polyethylene terephthalate (e.g. Dacron) prosthetic vascular grafts do not permit vessel ingrowth from the surrounding tissue due to too narrow or discontinuous ingrowth spaces. However, novel polyurethane prostheses, including those of Applicants, do not have such limitations, as their well-defined porosity and large pore size allow for the uninterrupted ingrowth of tissue. For example, see U.S. Pat. application Ser. No. 09/434,649; International Patent Applications PCT US97/27629 and WO 01/05333, all of which are commonly assigned to the Assignee of the present application.

Although these high porosity polyurethane grafts, as well as ePTFE grafts with very high internodular distances (100–150 μm), and high porosity Polyethylene terephthalate (e.g. Dacron) or similar grafts, may all allow for the improved ingrowth of tissue and cells, the level of healing that is desired throughout the graft wall is not observed. This has been shown to be due to the chronic deposition of impenetrable blood products, such as fibrin, onto/into the lumenal surface portion, thereby limiting ingrowth and healing to only the ablumenal or outer portions of the graft wall.

Accordingly, achievement of spontaneous healing of ePTFE, polyurethane, or other vascular prostheses by providing very high, angiopermissive porosities (for example, ±150 μm IND/pore size) and a permanent or degradable lumenal film to limit or control fibrin deposition and compaction is one goal.

As shown in FIGS. 1–4, prior research and design failed to properly recognize and overcome the deposition and compaction problem created by the buildup of hostile and impenetrable fibrin or other blood products on lumenal surfaces and lumenal portions. In FIGS. 1–4, graft model 12 comprises any of a plurality of materials, including for example, ePTFE 15, polyurethane 19, or Polyethylene terephthalate (e.g. Dacron) 22. As shown, these materials form a lumenal wall 28 (which is shown having multiple different material constructions for illustration only) having an ablumenal outer portion 33, outer surface 36, lumenal inner portion 40 and lumenal surface 44. In normal grafts of these or other materials there is a flow of blood 50 therethrough, which also forms a natural deposit of blood products 53, e.g., fibrin or other products. This blood product formation creates a barrier effect which prevents ablumenal and transmural tissue ingrowth. The barrier effect functionally extends from within the vascular (graft) lumen out into the lumenal wall to a substantial distance (as shown by arrows 68), in some instances greater than 50% of a wall thickness, causing serious degradation of healing and prevention of healthy ingrowth of various tissue types. Failure to heal may lead to rejection, stiffness and even malfunctioning.

Figure 5:
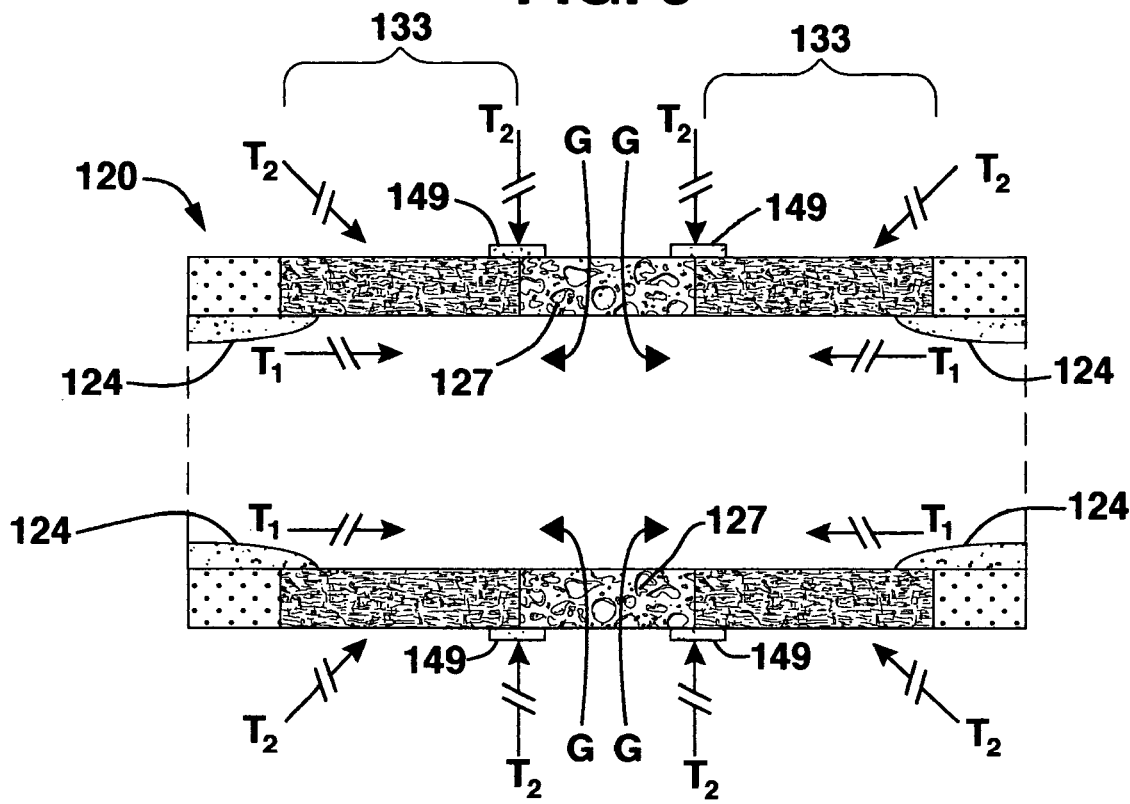
FIG. 5 is a sectional schematic view of a test segment of a graft model.

Efforts to determine the best technique to prevent this barrier included use of a hybrid test model graft 120, as shown in FIG. 5. This model graft was designed to prevent transanastomotic outgrowth (as shown at pannus growth portions 124 and arrows $T_1$) from a centrally located graft portion test segment 127, and thereby ensure that any endothelium observed on the test segment originated from transmural ingrowth only. In this example, model graft 120 uses isolating segments 133 of low porosity (30 μm) ePTFE around a high porosity material such as, for example, high porosity ePTFE, Polyethylene terephthalate (e.g. Dacron) or high porosity polyurethane to form a graft portion test segment 127. A sealant or film material 149 is placed between isolating and test segments to prevent tissue ingrowth between the two graft segments. This test demonstrated that the film material prevented or facilitated the prevention of unwanted growth via any anastomotic approach (arrows $T_1$) or transmural approach ($T_2$), while promoting the desired transmural ingrowth through the test segment as shown by arrows G. This test also demonstrated the inability of tissue to grow transmurally through a low porosity material ($T_2$).

Figure 6:
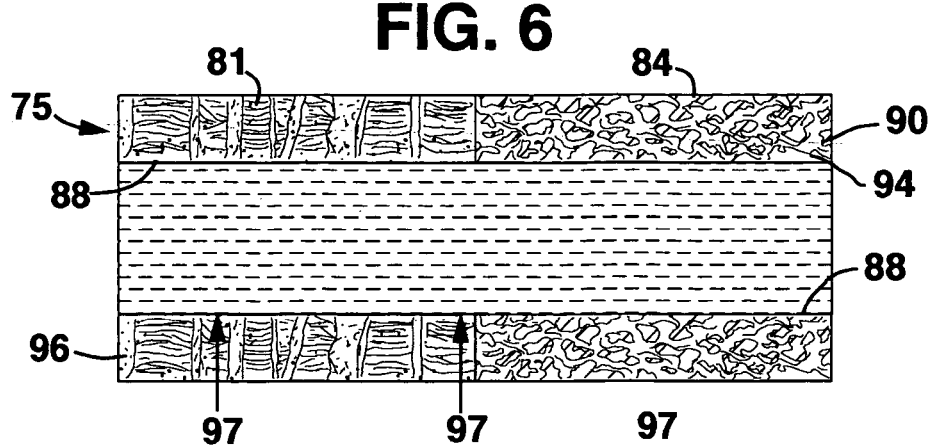
FIG. 6 is a sectional schematic view of a segment of a hybrid graft model illustrating the lack of fibrin buildup due to a first embodiment lumenal sealant.
Figure 7:
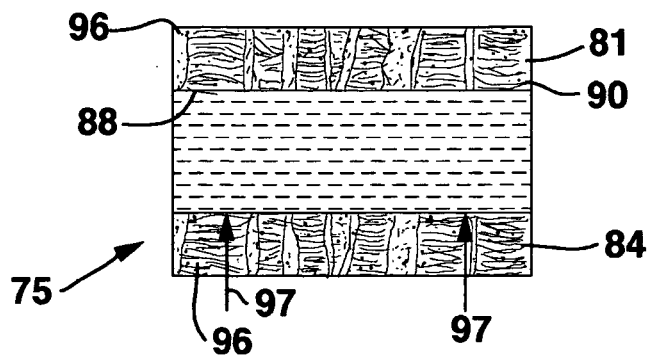
FIG. 7 is a sectional schematic view of a segment of an ePTFE graft model illustrating a first embodiment lumenal sealant.
Figure 8:
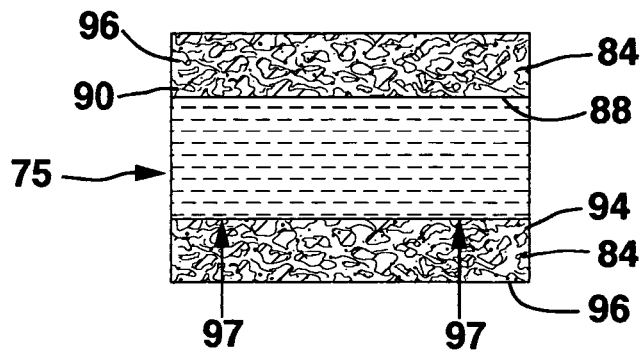
FIG. 8 is a sectional schematic view of a segment of a polyurethane graft model illustrating a first embodiment lumenal sealant.
Figure 9:
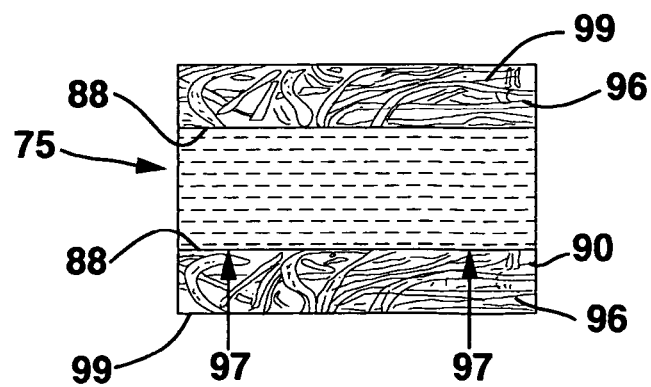
FIG. 9 is a sectional schematic view of a segment of a polyethylene terephthalate (e.g. Dacron) graft model illustrating a first embodiment lumenal sealant.

Applicants have discovered short- and long-term strategies, methods, and structures to overcome the problem of barriers to ablumenal tissue growth, i.e. the desired growth from outside the graft wall toward the lumen. In particular, in various embodiments, Applicants have realized that a thin skin or film of material may be applied within the inner lumenal portion 40 or 44 of an ingrowth-permissive synthetic graft with very advantageous results. FIGS. 6–9 illustrate sections of a schematic model graft 75 formed of any of the graft materials noted above, and further described below. In FIG. 6, model graft 75 (which is shown having multiple different material constructions for illustration only) illustrates two different types of graft wall material, ePTFE 81 and polyurethane 84—although other materials are possible if the configuration of the material allows for transmural tissue ingrowth. A thin film of permanent or degradable sealant material 88 is placed on a lumenal portion 90, which may include the lumenal surface 94, of the graft wall 96. This placement of film material 88 must functionally prevent the buildup of blood products, e.g. fibrin, without clogging the pores or other interstitial growth spaces within the graft wall structure. This promotes the transmural ingrowth of tissue ablumenally to the inner lumenal portion of the graft, as shown by arrows 97, which promotes improved healing and greater compliance and patency of the graft. FIGS. 7, 8, and 9 show graft walls 96 made of either high porosity ePTFE 81 (FIG. 7), high porosity polyurethane 84 (FIG. 8), or Polyethylene terephthalate (e.g. Dacron) 99 (FIG. 9).

Figure 10:
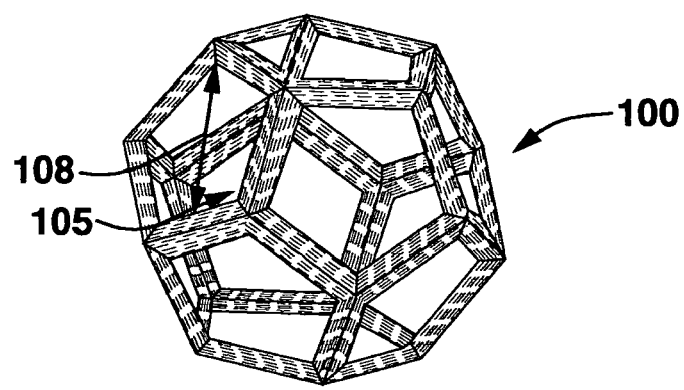
FIG. 10 is an exemplary unit cell of a porous foam-type material of a graft structure.

A preferred ePTFE material includes pore sizes having an internodular distance (IND) of greater than about 60 μm and more preferably about 60 to about 200 μm. A preferred porous foam-type of material includes a polyurethane material having spheroid interconnected pores formed as unit cells resembling dodecahedra, although various shapes may provide the desired characteristics. FIG. 10 shows a representation of one embodiment of a 50–250 μm diameter pore 100 having 20–150 μm diameter interconnecting windows 105, as shown by diameter line 108. A preferred Polyethylene terephthalate (e.g. Dacron), or other material, should be constructed (i.e. knitted, felt, or other technique) so that the porosity between fibers permits transmural growth substantially through to an inner lumenal portion. The wall thickness of grafts made according to this invention may be about 0.2–2 mm, with a preferred range of about 0.3–0.7 mm, and an overall graft diameter of between about 2–25 mm. The thickness of a solid sealant or film material may be in the range of 10–200 μm, with a preferred range of thickness of about 20–50 μm. Examples of suitable graft materials and constructions are shown in co-pending and commonly owned patent applications: U.S. Ser. No. 09/434,649; International Patent Applications PCT US97/27629 and WO 01/05333, each of which is incorporated by reference for such teaching.

The film material should span each pore of the surface of the graft wall lumenal portion, or at a selected depth—rather than filling each pore it contacts. For example, the film should function as if it were a thin piece of paper laying atop a sponge to prevent material penetration into the sponge pores below the paper. In a similar manner the film of sealant material acts as a spanning film rather than a filling sealant, so as to separate the blood from the tissue with as little thickness as possible or desired.

Figure 11:
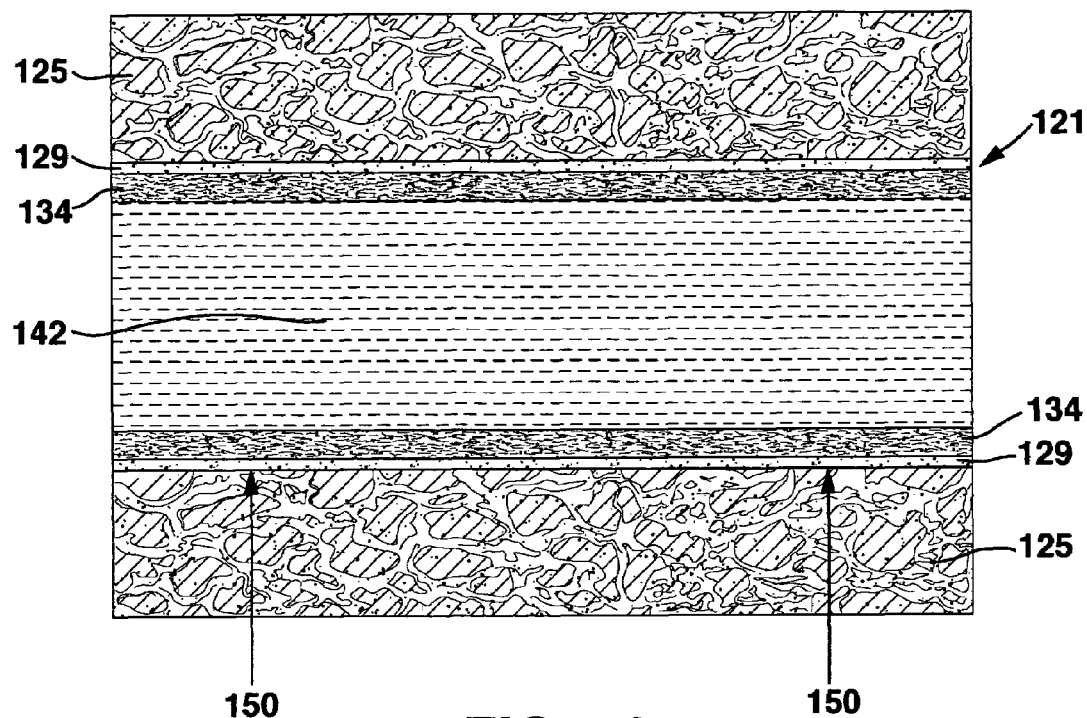
FIG. 11 is a sectional schematic view of a segment of a graft model illustrating a second embodiment lumenal sealant.

FIG. 11 shows another embodiment of improved graft prostheses 121 combining angio-permissive graft wall material 125 with a preferred film 129 at a lumenal portion of the wall structure, as described herein. Another material, referred to herein as an additional porous layer 134, provides either a porous structure or a surface having increased roughness as compared to film material 129. Layer 134 is designed to improve graft patency by creating a more anti-thrombogenic effect within the lumen 142. Tissue ingrowth lines 150 illustrate the depth to which transmural ingrowth occurs when this combination of ingrowth-permissive wall material and a preferred film is utilized.

Figure 12:
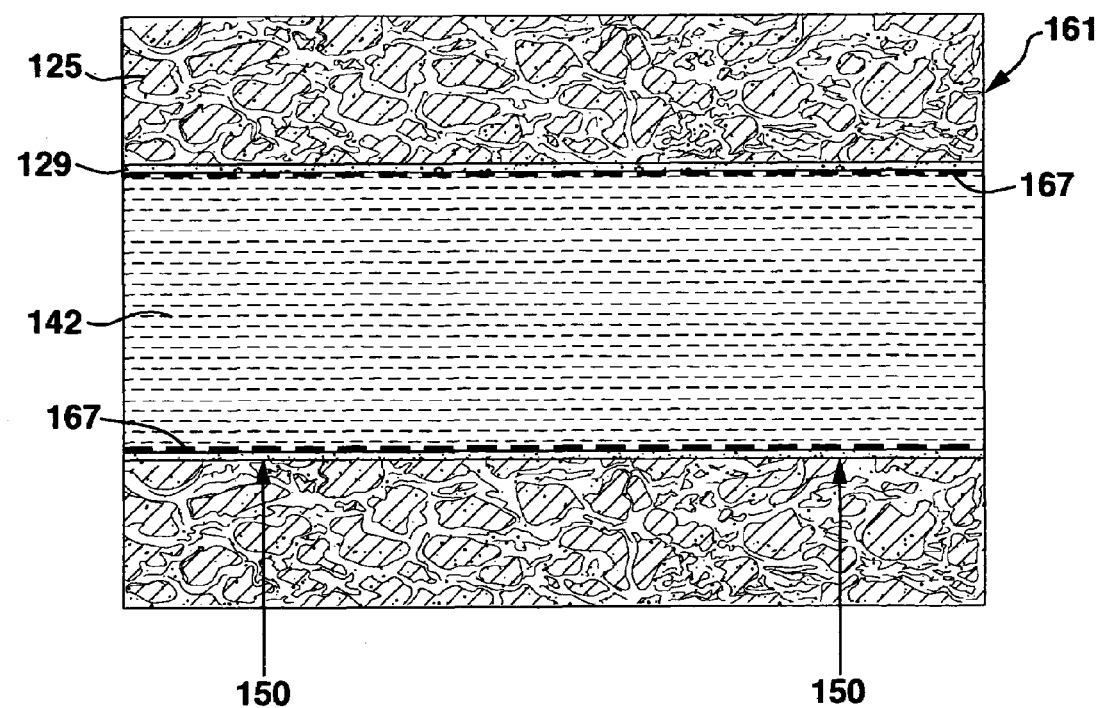
FIG. 12 is a sectional schematic view of a segment of a graft model illustrating a third embodiment lumenal sealant.

FIG. 12 shows a graft prosthesis 161 formed substantially similar to that of FIG. 11, except that wall structure 125 has a film material 129 that is covered or substantially coated with a thin anti-thrombotic surface 167, rather than a thicker porous structure as shown by structure 134 in FIG. 11.

Figure 13:
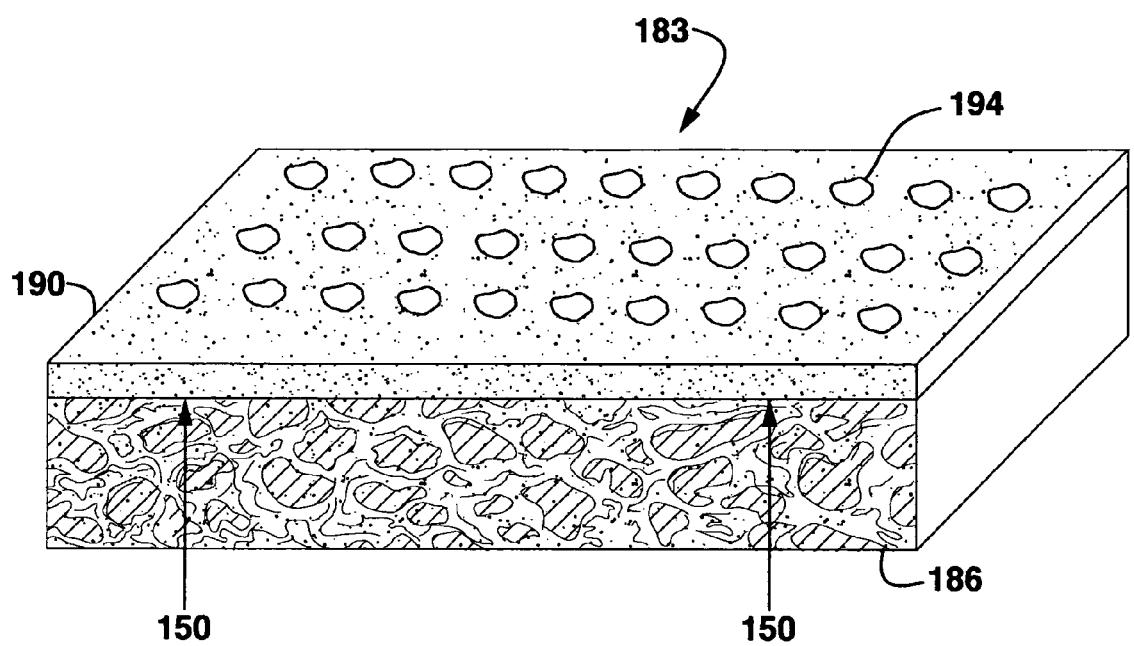
FIG. 13 is a sectional schematic view of a segment of a graft model illustrating a third embodiment lumenal sealant.

As noted herein, the sealant or film material may be a permanent, semi-permanent or intentionally degradable material. For example, in a large aortic-size graft prosthesis, it may be desirable to have a permanent film or a film having a degree of permanence which extends over considerable time in order to permit rapid and continuous muscle-like tissue ingrowth transmurally through the graft. For such prostheses, particularly that where flexibility is quite important to functionality, a permanent film might best facilitate such rapid transmural tissue ingrowth. However, in that or other applications, it may also be desirable to permit full tissue penetration transmurally into the lumenal portion of the graft. This may require a film having various thicknesses or a thickness designed to permit tissue penetration, transmurally, after a specified length of time. Another way of achieving this goal is to provide a film having a structure similar to that represented in FIG. 13. In this figure, graft prosthesis 183 comprises a graft wall material 186 which is an ingrowth-permissive material, such as those mentioned herein, and which has a film 190 which defines regions 194 of degradation over time which allow for the degradation of these areas to form communications between the ablumenal and lumenal surfaces and thereby promote full transmural ingrowth by tissue. It is recognized that regions 194 are shown in a representative fashion only for illustration of this concept, and may comprise various patterns or area configurations. Such regions 194 may also prevent the sloughing off of large pieces of degradable material as it naturally degrades over the desired time. Of course, preferred degradation times will vary according to the recipient of the graft prosthesis and the type of material within the graft.

The material which forms the film of Applicants is preferably a polymeric film which is deposited in as thin a structure as possible, but strong enough to withstand the rigors of the biological system within which the graft is placed. The film is designed to obstruct rather than clog the pores of the lumenal portion of the graft, and by not necessarily penetrating the pores the film permits rapid and effective transmural ingrowth of tissue to promote healing throughout the width of the graft wall. If either the graft wall is made of ingrowth-prohibitive material or the lumenal portion of the graft wall is sealed off or clogged by either a sealant material (unlike that preferably described herein as a film) or by blood products such as compacted fibrin or the like, then the graft prosthesis will fail to demonstrate the advantageous results and characteristics as described by Applicants. Alternatively, use of a graft wall material which is ingrowth-permissive so that a complete transgression from the outer wall into the lumen of the graft is permitted for capillaries, and the type of film described herein is provided at a lumenal portion to facilitate and encourage rapid ingrowth of the capillaries and tissue transmurally, then the combination will result in improved outcomes and higher acceptance of the graft by the recipient or host body.

The permanent or semi-permanent sealants or films of this invention include medical grade polyurethanes, such as for example those known by the names Pellethane, M48, ElastEon, Bionate, or other medical grade polyurethanes marketed under various trade names. The method of application of the material includes application of the polymer solution to a lumenal portion or surface and then solidification of the polymer by evaporation and/or precipitation. Anti-thrombogenicity may be enhanced by the covalent immobilization of heparin onto the lumenal surface after placement of the material.

EXAMPLE 1

A 150 μm polyurethane and 150 μm internodular diameter ePTFE with plus or minus ±50 μm polyurethane lumenal film skin was provided. Acrylic acid/acrylamide hydrogel and ethylene diamine (EDA) bridge and a periodate oxidized heparin was provided as well. The results indicated an improvement in tissue (including capillaries and arterioles) ingrowth when compared to the ingrowth obtained in similar prostheses without the lumenal skin. In particular, the ingrowing vessels occupied the full extent of the graft wall thickness (up to the ablumenal side of the lumenal film) of grafts provided with a lumenal film. When the lumenal film was absent, a thick band of compacted fibrin (and other blood constituents) was observed in the lumenal third of the graft wall. This fibrin layer impeded and restricted the further ingrowth of tissue, and thereby limited the healing to the outer two-thirds of the graft wall.

Medical grade polysiloxanes, for example that known as PDMS (trade name NuSil) or other branded medical grade polysiloxanes are also useful as a film. Application of the monomer or prepolymer to the lumenal portion or surface is accomplished. Then, solidification of the polymer by reaction with an initiator occurs. Silicone films are permeable to oxidation and carbon dioxide and may be used (when compared to essentially oxygen-impermeable materials e.g. polyurethanes) to determine the effect of hypoxia on the healing of sub-sealant regions. Hypoxia is one of the possible mechanisms which are involved with the advancements of this invention.

The degradable films or sealants discussed herein include degradable polyurethanes, polyethylene oxide-polylactic acid copolymers and degradable hydrogels. Although most polyurethanes are designed to be biostable, i.e. to resist chemical degradation in vivo, there are instances for this application where biodegradability may be desired. One class of such materials include the polyesters (polyglycolic acid, polylactic acid, polycaprolactone, polyhydroxybuterate, polyortoesters, etc.), polyanhydrides (poly (sebasic acid-hexadecanoic acid anhydride)), and polyiminocarbonates. Another class of degradable materials includes synthetic hydrogels, which may be simply non-degradable hydrogel monomers incorporating degradable sites in their chains and/or using degradable crosslinkers. One example includes synthetic hydrogels (such as polyethyleneglycol, etc.) that are cross-linked by hydrolytically or enzymatically cleavable compounds in such a way that cleavage of the crosslinker results in the degradation of the crosslinked polymer.

Another class of biodegradable polymers includes the biologically derived hydrogels such as polyamino acids and polysaccharides. Synthetic hydrogels include a number of other water soluble polymers which may be used to form hydrogel films by a wide range of crosslinking reactions. These materials include polyethyleneglycol (PEG), polyvinyl alcohol (PVAL), polyvinyl pyrrolidone (PVP), polyethyleneimine (PEI), polyhydroxyethyl methacrylate (PHEMA) family, polyacrylic acid (Paac), polyacrylamide (Paam), etc. Crosslinking may be effected by: inclusion of a di or multi-vinyl compounds during polymerization and reaction of di-or multifunctional compounds with side groups of preformed linear polymers. Another class of degradable polymers are of biologic origin. When they occur in their hydrated insoluble state, these materials may also be classified as hydrogels. Both carbohydrates (hyaluronic acid, cellulose, alginates) and proteins (collagen, gelatin) may be immobilized as a hydrogel films on the surface of grafts by crosslinking with a variety of compounds.

It is, therefore, a goal of Applicants to achieve spontaneous healing and lumenal endothelialization of ePTFE, polyurethane, Polyethylene terephthalate (e.g. Dacron) or other vascular prostheses by providing very high angiopermissive porosities (±150 µm IND/pore size) and permanent or degradable lumenal portion films to better control the deposition and compaction of blood products. The film would initially inhibit, prevent, or control the deposition of impenetrable fibrin or other products in the pores of the wall structure, thereby allowing uninterrupted tissue ingrowth from the ablumenal surface. Any degradable film material would be dissolved or otherwise eliminated through biologic action, while allowing the population and proper healing of the lumenal surface by transmural tissue ingrowth. In addition to the concepts disclosed above, Applicants believe that this novel and non-obvious lumenal sealant or film, having possible degradation features designed therein, provides a temporary shield against plasma insituization as well as a temporary modality to create controlled hypoxia during the healing process, thus permitting proper penetration of desired tissues in the desired manner, and obviating creation of undesirable barriers to such healing.

No other recognition of such a problem and solutions is known by Applicants, nor have Applicants noted the recognition by any other of the underlying cause of the failure of these grafts to properly heal due to the buildup from the lumenal surface creating a hostile environment for adequate transmural tissue ingrowth.

We claim:

1. A vascular graft prosthesis comprising:
a polymeric tubular structure having an ablumenal surface and having a porous wall having pores and with interstices arranged to permit transmural ingrowth of tissue from the ablumenal surface substantially through the full thickness of the wall;
the wall having a lumenal surface forming a channel for blood flow; and
a layer of sealant material on a portion of the wall forming a lumenal wall surface but not filling the pores, the sealant layer being capable of retarding formation of a natural barrier to translumenal tissue ingrowth from the ablumenal surface, the sealant material having a degradable property so that the material will degrade in a predetermined manner or time.

2. The vascular graft prosthesis of claim 1 wherein the polymeric tubular structure wall material is selected from the group consisting of polyurethane, expanded polytetrafluoroethylene, and Polyethylene terephthalate (Dacron).

3. The vascular graft prosthesis of claim 1, wherein the tubular structure comprises interconnected shaped pores having an internodular distance of greater than about 60 µm.

4. The vascular graft prosthesis of claim 1, wherein the tubular structure comprises interconnected shaped pores having diameters of greater than about 60 µm and less than about 200 µm.

5. The vascular graft prosthesis of claim 1, wherein the tubular structure comprises a polymer structure having a wall, and interconnecting shaped pores in the tube wall; wherein porosity is optimized to maximize cellular ingrowth.

6. The vascular graft prosthesis of claim 1 in which the tubular structure comprises ingrowth matrix material.

7. A vascular graft prosthesis comprising:
a polymeric tubular structure having an ablumenal surface and having a porous wall having pores and with interstices arranged to permit transmural ingrowth of tissue from the ablumenal surface substantially through the full thickness of the wall;
the wall having a lumenal surface forming a channel for blood flow; and a layer of sealant material on a portion of the wall forming a lumenal wall surface but not filling the pores, the sealant layer being capable of retarding formation of a natural barrier to translumenal tissue ingrowth from the ablumenal surface, the sealant material comprising a material selected from the group consisting of polyurethane, a polysiloxane polymer, segmented polyurethane, lactic/glycolic polymers, polyethylene glycol-polylactic acid copolymer, synthetically derived hydrogels, polyethylene glycol hydrogels, and biologically derived hydrogels.

8. A method of promoting healing in a vascular graft prosthesis comprising the steps of:
   a. providing a vascular graft having a lumen and a lumenal wall configured with ingrowth-permissive interstices; and
   b. applying a degradable sealant material to a surface of the lumenal wall as a spanning film but not filling the interstices to maintain separation of blood within the vascular graft between the lumen interior and the growth-permissive interstices of the lumenal wall to prevent formation of a natural barrier to tissue ingrowth and to promote healing of tissue through substantially the entire graft wall thickness.

9. An implantable wall structure designed and configured for implant into mammalian tissue and having a blood-contacting surface, the wall structure having
   interconnected wall material designed for transmural tissue ingrowth and healing; and
   a thin film of sealant material placed on the blood-contacting surface but not clogging the interconnected wall material, the film having a degradable material construction and composition so as to promote desired healing of tissue adjacent to and within the wall structure and to retard formation of a natural barrier to tissue growth into the interconnected wall material.

10. The wall structure of claim 9 in which at least a part of the sealant material is enzymatically degradable.

11. The wall structure of claim 9, wherein the sealant material comprises a material selected from the group consisting of polyurethane, a polysiloxane polymer, segmented polyurethane, lactic/glycolic polymers, polyethylene glycol-polylactic acid copolymer, synthetically derived hydrogels, polyethylene glycol hydrogels, and biologically derived hydrogels.

12. The wall structure of claim 9, wherein the wall material is selected from the group consisting of polyurethane, expanded polytetrafluoroethylene, and Polyethylene terephthalate (Dacron).

13. A vascular graft prosthesis comprising:
   a polymeric tubular structure having a wall defining an ablumenal surface and a lumen for blood flow;
   interconnected shaped pores in the wall; and
   a film layer of sealant material on the lumenal wall surface but not clogging the pores, which layer reduces the buildup of natural fibrin on the lumenal wall surface and into the pores and facilitates transmural growth of tissue from the ablumenal surface into the interconnected shaped pores, at least a part of the sealant material being enzymatically degradable.

14. The tubular structure of claim 13, wherein the wall material is selected from the group consisting of polyurethane, expanded polytetrafluoroethylene, and Polyethylene terephthalate (Dacron).

15. A vascular graft prosthesis comprising:
   a polymeric tubular structure having a wall defining an ablumenal surface and a lumen for blood flow;
   interconnected shaped pores in the wall; and
   a film layer of sealant material on the lumenal wall surface but not clogging the pores, which layer reduces the buildup of natural fibrin on the lumenal wall surface and into the pores and facilitates transmural growth of tissue from the ablumenal surface into the interconnected shaped pores, wherein the sealant material comprises a material selected from the group consisting of polyurethane, a polysiloxane polymer, segmented polyurethane, lactic/glycolic polymers, polyethylene glycol-polylactic acid copolymer, synthetically derived hydrogels, polyethylene glycol hydrogels, and biologically derived hydrogels.

16. A vascular graft prosthesis comprising:
   a tubular structure having a wall made of biocompatible highly porous material with interconnected shaped pores in the wall, the wall defining a lumen for blood flow; and
   a thin spanning layer of a degradable sealant material on the lumenal wall surface which reduces the buildup of natural fibrin on the lumenal wall surface and into the interconnected shaped pores and facilitates transmural growth of tissue into the interconnected shaped pores.

17. The tubular structure of claim 16 in which at least a part of the sealant material is enzymatically degradable.

18. The tubular structure of claim 16, wherein the wall material is selected from the group consisting of polyurethane, expanded polytetrafluoroethylene, and Polyethylene terephthalate (Dacron).

19. A vascular graft prosthesis comprising:
   a tubular structure having a wall made of biocompatible highly porous material with interconnected shaped pores in the wall, the wall defining a lumen for blood flow; and
   a thin spanning layer of sealant material on the lumenal wall surface which reduces the buildup of natural fibrin on the lumenal wall surface and into the interconnected shaped pores and facilitates transmural growth of tissue into the interconnected shaped pores, wherein the sealant material comprises a material selected from the group consisting of polyurethane, a polysiloxane copolymer, segmented polyurethane, lactic/glycolic polymers, polyethylene glycol-polylactic acid copolymer, synthetically derived hydrogels, polyethylene glycol hydrogels, and biologically derived hydrogels.

20. A vascular graft prosthesis comprising:
   a tubular structure having a wall made of biocompatible highly porous material with interconnected shaped pores in the wall, the wall defining a lumen for blood flow and having a lumenal surface and an ablumenal surface; and
   a film of degradable sealant material carried by the wall which reduces the buildup of natural blood products at and adjacent to the lumenal wall surface but which leaves the interconnected shaped pores of the wall substantially unplugged by sealant material to facilitate transmural growth of tissue from the ablumenal surface.

21. A biocompatible graft material suitable for use in a mammalian vascular system, comprising:
   a volume of graft material having a length, width and thickness suitable for shaping into a tubular vascular graft and having a first surface adapted to form a lumenal surface for blood contact;
   said graft material comprising a first high porosity structural material for providing pathways through which transmural tissue growth may occur;

a degradable sealant material deposited on a the graft material first surface to prevent the buildup of natural fibrin at and adjacent to said first surface of the graft material but which leaves the pathways for transmural tissue growth substantially unplugged by sealant material to facilitate transmural growth of tissue through a thickness of the graft material; and said graft material having a second structural material on a first surface of said sealant material.

22. The graft of claim 21 wherein the second structural material is highly porous.

23. A vascular graft prosthesis having a wall structure configured to optimize transmural tissue ingrowth and a sealant-like material, the wall structure comprising a generally tubular polymeric wall having an ablumenal surface free of sealant-like material and which allows uninterrupted cellular growth, the wall having a lumenal surface for contact with blood; and the sealant-like material forming a degradable film on a the lumenal surface configured to keep blood products from clogging ablumenal portions of the wall structure and to promote transmural tissue ingrowth.

24. The wall structure of claim 23 in which at least a part of the sealant-like material is enzymatically degradable.

25. The vascular graft prosthesis of claim 23 wherein the wall structure is selected from the group consisting of polyurethane, expanded polytetrafluoroethylene, and Polyethylene terephthalate (Dacron).

26. A vascular graft prosthesis having a wall structure configured to optimize transmural tissue ingrowth and a sealant-like material, the wall structure comprising a generally tubular polymeric wall having an ablumenal surface free of sealant-like material and which allows uninterrupted cellular growth, the wall having a lumenal surface for contact with blood: and the sealant-like material forming a film on a the lumenal surface configured to keep blood products from clogging ablumenal portions of the wall structure and to promote transmural tissue ingrowth, wherein the sealant-like material comprises a material selected from the group consisting of polyurethane, a polysiloxane polymer, segmented polyurethane, lactic/glycolic polymers, polyethylene glycol-polylactic acid copolymer, synthetically derived hydrogels, polyethylene glycol hydrogels, and biologically derived hydrogels.

27. A vascular graft prosthesis having a wall structure configured to optimize transmural tissue ingrowth and a sealant-like material, the wall structure comprising a generally tubular polymeric wall substantially free of sealant-like material and which allows uninterrupted cellular growth, the wall having a lumenal surface for contact with blood; and the sealant-like material forming a degradable film on the lumenal surface configured to keep blood products from clogging ablumenal portions of the wall structure and to promote transmural tissue ingrowth, the film of sealant-like material having a thickness in the range of about 10–200 μm.

28. A vascular graft prosthesis having a wall structure configured to optimize transmural tissue ingrowth and a sealant-like material, the wall structure comprising a generally tubular polymeric wall substantially free of sealant-like material and which allows uninterrupted cellular growth, the wall having a lumenal surface for contact with blood; and the sealant-like material forming a degradable film on the lumenal surface configured to keep blood products from clogging ablumenal portions of the wall structure and to promote transmural tissue ingrowth, the film of sealant-like material having a thickness in the range of about 10–50 μm.

29. A method of manufacturing a vascular graft prosthesis, comprising the steps of:

arranging a tubular structure having a wall made of biocompatible highly porous material with interconnected shaped pores in the wall and having a lumenal surface and an ablumenal surface; and placing a thin spanning layer of a degradable sealant material on the lumenal surface of the wall but not clogging the pores, which layer reduces the buildup of natural blood products or other material within the pores of the wall and facilitates transmural growth of tissue from the ablumenal surface substantially through the full thickness of the highly porous material.

30. The method of claim 29 comprising the further step of configuring another layer of material on the thin spanning layer of material to form an anti-thrombogenic layer as a lumenal wall layer.

31. A vascular graft prosthesis comprising:

a polymeric tubular structure having a porous wall with interstices arranged to permit transmural ingrowth of tissue substantially through the full thickness of the wall, the tubular structure comprising having a wall thickness in the range of 0.2–2 mm; and a layer of sealant material on a portion of the wall forming a lumenal wall surface, the sealant material having a degradable property so that the material will degrade in a predetermined manner or time.

32. A vascular graft prosthesis comprising:

a polymeric tubular structure having a porous wall with interstices arranged to permit transmural ingrowth of tissue substantially through the full thickness of the wall, the tube structure having interconnected shaped pores having diameters of greater than about 60 μm and less than about 200 μm and an average diameter in a range of 100–200 μm.; and a layer of sealant material on a portion of the wall forming a lumenal wall surface.

33. A vascular graft prosthesis comprising:

a polymeric tubular structure having a porous wall with interstices arranged to permit transmural ingrowth of tissue substantially through the full thickness of the wall, the tubular structure having pores with an average diameter in a range of 0.1–3.0 mm, allowing for un-interrupted tissue growth; and wherein the overall graft diameter is between about 2–25 mm, and a layer of degradable sealant material on a portion of the wall forming a lumenal wall surface.

34. An implantable wall structure designed for implant into mammalian tissue, having:

a wall structure with interconnected wall material designed for transmural tissue ingrowth and healing; and a thin film of sealant material placed on the wall structure and having a degradable material construction and composition so as to promote desired healing of tissue adjacent to and within the wall structure, at least a part of the sealant material being hydrolytically degradable.

35. An implantable wall structure designed for implant into mammalian tissue, having:
a wall structure with interconnected wall material designed for transmural tissue ingrowth and healing; and
a thin film of sealant material placed on the wall structure and having a degradable material construction and composition so as to promote desired healing of tissue adjacent to and within the wall structure, the film having a thickness of between about 10–200 μm.

36. An implantable wall structure designed for implant into mammalian tissue, having:
a wall structure with interconnected wall material designed for transmural tissue ingrowth and healing; and
a thin film of sealant material placed on the wall structure and having a degradable material construction and composition so as to promote desired healing of tissue adjacent to and within the wall structure, the film having a thickness of between about 10–50 μm.

37. A vascular graft prosthesis comprising:
a polymeric tubular structure having a wall;
interconnected shaped pores in the wall; and
a film layer of sealant material on a portion of the wall forming a lumenal wall surface which reduces the buildup of natural fibrin on the lumenal wall surface and facilitates transmural growth of tissue, at least a part of the sealant material being hydrolytically degradable.

38. A vascular graft prosthesis comprising:
a polymeric tubular structure having a wall;
interconnected shaped pores in the wall; and
a film layer of sealant material on a portion of the wall forming a lumenal wall surface which reduces the buildup of natural fibrin on the lumenal wall surface and facilitates transmural growth of tissue, the film being degradable and having a thickness of between about 10–200 μm.

39. A vascular graft prosthesis comprising:
a polymeric tubular structure having a wall;
interconnected shaped pores in the wall; and
a film layer of sealant material on a portion of the wall forming a lumenal wall surface which reduces the buildup of natural fibrin on the lumenal wall surface and facilitates transmural growth of tissue, the film being degradable and having a thickness of between about 10–50 μm.

40. A vascular graft prosthesis comprising:
a tubular structure having a wall made of biocompatible highly porous material with interconnected shaped pores in the wall; and
a thin spanning layer of a degradable sealant material on a portion of the wall forming a lumenal wall surface which reduces the buildup of natural fibrin on the lumenal wall surface and facilitates transmural growth of tissue, the layer of sealant material being hydrolytically degradable.

41. A vascular graft prosthesis comprising:
a tubular structure having a wall made of biocompatible highly porous material with interconnected shaped pores in the wall; and
a thin spanning layer of sealant material on a portion of the wall forming a lumenal wall surface which is degradable and which reduces the buildup of natural fibrin on the lumenal wall surface and facilitates transmural growth of tissue, the layer of sealant material, the thin spanning layer of sealant material having a thickness of between about 10–200 μm.

42. A vascular graft prosthesis comprising:
a tubular structure having a wall made of biocompatible highly porous material with interconnected shaped pores in the wall; and
a thin spanning layer of sealant material on a portion of the wall forming a lumenal wall surface which reduces the buildup of natural fibrin on the lumenal wall surface and facilitates transmural growth of tissue, the thin spanning layer of sealant material being degradable and having a thickness of between about 10–50 μm.

43. A vascular graft prosthesis having a wall structure configured to optimize transmural tissue ingrowth, comprising:
a polymeric wall structure which allows uninterrupted cellular growth; and
a film of sealant-like material on a lumenal portion of the graft configured to keep blood products from clogging ablumenal portions of the wall structure and to promote transmural tissue ingrowth, at least a part of the sealant-like material being hydrolytically degradable.

44. A vascular graft prosthesis comprising:
a polymeric tubular structure having a porous wall formed of a material selected from the group consisting of polyurethane and polyester, with interstices arranged to permit transmural ingrowth of tissue substantially through the full thickness of the wall;
the wall having a lumenal surface forming a channel for blood flow; and
a layer of sealant material on a portion of the wall forming a lumenal wall surface but not filling the pores, the sealant layer being degradable and being capable of retarding formation of a natural barrier to translumenal tissue ingrowth.

45. A method of promoting healing in a vascular graft prosthesis comprising the steps of:
a. providing a vascular graft of a material selected from the group consisting of polyurethane and polyester, the graft having a lumen and a lumenal wall configured with ingrowth-permissive interstices; and
b. applying a degradable sealant material to a surface of the lumenal wall as a spanning film but not filling the pores to maintain separation of blood within the vascular graft between the lumen interior and the growth-permissive interstices of the lumenal wall to prevent formation of a natural barrier to tissue ingrowth and to promote healing of tissue through substantially the entire graft wall thickness.

46. A vascular graft prosthesis comprising:
a tubular structure formed of polyurethane or polyester, the structure having a wall defining an ablumenal surface and a lumen for blood flow;
interconnected shaped pores in the wall; and
a film layer of degradable sealant material on the lumenal wall surface but not clogging the pores, which layer reduces the buildup of natural fibrin on the lumenal wall surface and into the pores and facilitates transmural growth of tissue from the ablumenal surface into the interconnected shaped pores.

* * * * *